United States Patent
Bradley et al.

(10) Patent No.: US 6,931,281 B2
(45) Date of Patent: Aug. 16, 2005

(54) METHOD AND APPARATUS FOR MONITORING MYOCARDIAL CONDUCTION VELOCITY FOR DIAGNOSTICS OF THERAPY OPTIMIZATION

(75) Inventors: Kerry Bradley, Glendale, CA (US); Jeffery D. Snell, Chatsworth, CA (US)

(73) Assignee: Pacesetter, Inc., Sylmar, CA (US)

( * ) Notice: Subject to any disclaimer, the term of this patent is extended or adjusted under 35 U.S.C. 154(b) by 609 days.

(21) Appl. No.: 10/121,523

(22) Filed: Apr. 12, 2002

(65) Prior Publication Data

US 2003/0195580 A1 Oct. 16, 2003

(51) Int. Cl.$^7$ .............................................. A61N 1/362
(52) U.S. Cl. .............................. 607/9; 607/17; 607/28
(58) Field of Search ........................ 607/9, 25, 27–28, 607/4, 17, 18

(56) References Cited

U.S. PATENT DOCUMENTS

| | | | |
|---|---|---|---|
| 4,228,803 A | 10/1980 | Rickards | 128/419 PG |
| 4,712,555 A | 12/1987 | Thornander et al. | 128/419 PG |
| 4,759,367 A | 7/1988 | Callaghan | 128/419 PG |
| 4,858,610 A | 8/1989 | Callaghan et al. | 128/419 PG |
| 5,243,981 A | 9/1993 | Hudrlik | 607/11 |
| 6,301,496 B1 | 10/2001 | Reisfeld | 600/407 |
| 6,473,647 B1 * | 10/2002 | Bradley | 607/27 |

FOREIGN PATENT DOCUMENTS

EP  0 839 554 A2 * 5/1998 ............ A61N/1/37

OTHER PUBLICATIONS

Halliday, David & Resnick, Robert, Physics—Part I, Chapter "3–3: Average Velocity", John Wiley & Sons, (c) 1977, pp. 31–32.*

* cited by examiner

*Primary Examiner*—Carl Layno

(57) ABSTRACT

A cardiac stimulation device and method to measure a myocardial conduction time and to store its long-term running average. A multipolar lead is used to deliver a stimulation pulse from a tip electrode and detect the evoked response after it has propagated to a ring electrode. The time between the stimulation pulse and a detected feature of the evoked response is determined as the myocardial conduction time. A long-term average myocardial conduction time is calculated by averaging on the order of five hundred stimulated cardiac cycles, and a running average is stored in memory. Shifts in the myocardial conduction time may be used for monitoring disease progression or the long-term response to a treatment.

33 Claims, 4 Drawing Sheets

METHOD AND APPARATUS FOR MONITORING MYOCARDIAL CONDUCTION VELOCITY FOR DIAGNOSTICS OF THERAPY OPTIMIZATION

FIELD OF THE INVENTION

The present invention relates generally to an implantable cardiac stimulation device and, more specifically, to a method for storing a long-term average myocardial conduction velocity as a diagnostic measure of the physiological condition of the heart for use in monitoring heart disease or optimizing a delivered therapy.

BACKGROUND OF THE INVENTION

In a normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (A-V) node and a ventricular conduction system causing a depolarization known as an R-wave and the resulting ventricular chamber contractions.

The intrinsic heart rate is primarily controlled by the sympathetic and parasympathetic components of the autonomic nervous system. Both components have nerve fibers terminating on the sinus node. Increased sympathetic activation (increased sympathetic tone) increases the heart rate as well as the conduction velocity of action potentials through the heart. Increased parasympathetic tone, also referred to as "vagal tone" since the parasympathetic nerves enter the heart via the vagus nerve, decreases the heart rate and decreases conduction velocity through the heart. Other factors such as circulating hormones and heart wall stretch will also influence heart rate and conduction. Though not fully understood, cardiovascular diseases and other physiological states may alter sympathetic tone, parasympathetic tone, and circulating hormonal levels and thus alter the heart tissue conduction velocity.

Disruption of the natural pacemaking and conduction system as a result of aging or disease can be successfully treated by artificial cardiac pacing. Implantable cardiac stimulation devices, including pacemakers and implantable defibrillators, deliver rhythmic electrical pulses or other anti-arrhythmia therapies to the heart at a desired energy and rate via electrodes implanted in contact with the heart tissue. One or more heart chambers may be electrically stimulated depending on the location and severity of the conduction disorder.

Cardiac stimulation devices have a great number of adjustable parameters that must be tailored to a particular patient's therapeutic needs. The process of selecting the optimal parameter settings can be lengthy and complicated. Recent clinical evidence supports the use of multichamber stimulation devices for improving hemodynamic efficiency in patients with congestive heart failure. With an increasing number of indications for cardiac pacing, the number of programmable parameters required for tailoring individual patient therapies further complicates the programming process.

Without feedback on the effect of programmed parameters, the physician faces a challenge in selecting the most effective pacing regimen. It would be advantageous, therefore, to provide the physician with physiological data that reflects the effect of an applied therapy, whether the therapy is an implanted stimulation device or a drug therapy.

Observation of changes related to sympathetic and vagal tone, which are known to occur with certain disease processes, may be one way to monitor the response to a therapy. For example, high, relatively constant sympathetic tone and low vagal tone are known chronic conditions in patients with heart failure. Unusual circadian changes in myocardial conduction velocity may be observed in patients with heart failure. Long-term monitoring of myocardial conduction velocity, therefore, would allow conduction changes to be detected that might be indicative of a change in heart condition. This monitoring would allow tracking of disease progression or the response to drug therapy or programmed pacing parameters.

A method for adjusting pacemaker parameters based on a measured myocardial conduction time has been proposed; however, the adjustments are made based on relatively short-term changes in conduction time, for example a change measured over three cardiac cycles. Since the physiological response to a change in drug therapy or programmed pacing parameters may not be instantaneous but may occur over an extended period of time, long-term monitoring of a physiological parameter reflective of the heart condition is desirable.

A device and method for long-term monitoring of myocardial conduction velocity, therefore, would improve the physician's ability to monitor a patient's disease state or therapy response. Such a method would preferably allow myocardial conduction data to be collected in an ongoing, day-to-day basis during a patient's normal activities. A physician may then examine the collected data for any shifts in long-term average myocardial conduction velocity and use this information in diagnosing the patient's heart condition and selecting treatments.

SUMMARY OF THE INVENTION

The present invention addresses these needs by providing an implantable cardiac stimulation device capable of measuring and storing myocardial conduction velocity. Myocardial conduction velocities may be stored over time in a histogram or log to provide long-term running average conduction velocity data for assessing the autonomic tone of the heart in patients having chronic heart conditions.

The foregoing and other features of the present invention are realized by providing an implantable cardiac stimulation device and associated electrodes for delivering stimulation pulses, sensing a propagated evoked response, and determining associated time intervals that quantify a myocardial conduction time. A preferred embodiment of the stimulation device includes a control system for controlling the operation of the device; a set of leads, which connect cardiac electrodes to the stimulation device for receiving cardiac signals and for delivering atrial and ventricular stimulation pulses; a set of sensing circuits comprised of sense amplifiers for sensing and amplifying the cardiac signals; a data acquisition system, such as an A/D converter, for sampling cardiac signals such that the time that a propagated evoked response is sensed may be determined; and pulse generators for generating atrial and ventricular stimulation pulses. The stimulation device includes memory for storing operational parameters for the control system, such as stimulation parameter settings and timing intervals, as well as for storing myocardial conduction velocity data. The device also includes a telemetry circuit for communicating with an external programmer.

When operating according to a preferred embodiment, a stimulation pulse of sufficient energy to depolarize the heart is delivered in a unipolar fashion using a tip electrode of a bipolar lead. The depolarization, known as an "evoked response," is sensed in a unipolar fashion using a ring electrode located on the same lead, a given distance from the tip electrode such that the propagating depolarization arrives at the ring electrode approximately 15 to 150 ms after delivery of the stimulation pulse. A characteristic feature of the sensed depolarization signal, such as a maximum negative slope, is detected as a waveform timing marker. The time interval between the delivered stimulation pulse and the detected waveform timing marker is determined as the myocardial conduction time. The myocardial conduction velocity is the known inter-electrode distance divided by the conduction time.

Preferably, a running average of the myocardial conduction velocity is determined. Such an average may be determined for a given number of heart beats, for example on the order of 500 to 5,000 heart beats. The average myocardial conduction velocity may be stored in memory on a periodic basis, along with the corresponding time of day, average pacing rate, activity level, or other desired parameters, in a data log or histogram format.

In one embodiment, the conduction velocity may be determined as a function of heart rate. Since the conduction time may be affected by the heart rate, multiple running averages of conduction velocity based on the heart rate may be determined. Alternatively, the running average conduction velocity may be computed as a ratio to the heart rate.

The stored conduction velocity data may be downloaded to an external device for analysis by a clinician. Shifts in the long-term average myocardial conduction velocity may indicate a change in disease state, a response to a drug therapy, or the response to a change in programmed stimulation parameters.

In another embodiment, a multi-electrode lead is used to measure myocardial conduction velocities between multiple sites of the heart tissue. Differences in conduction velocities associated with different segments of the myocardial tissue may be used in selecting a preferred stimulation site and may allow detection of local ischemia. Stimulation parameters or stimulation site may then be adjusted such that local ischemia is avoided or alleviated.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

DETAILED DESCRIPTION OF PREFERRED EMBODIMENTS

The following description is of a best mode presently contemplated for practicing the invention. This description is not to be taken in a limiting sense but is made merely for the purpose of describing the general principles of the invention. In the description of the invention that follows, like numerals or reference designators will be used to refer to like parts or elements throughout. The present invention is directed at providing a long-term running average of the myocardial conduction velocity of an evoked response for the purposes of monitoring disease progress or optimizing a medical or stimulation therapy. A general cardiac stimulation device will be described in conjunction with FIGS. 1 and 2, in which the features included in the present invention could be implemented. It is recognized, however, that numerous variations of such a device exist in which the methods included in the present invention could be implemented without deviating from the scope of the present invention.

Figure 1:
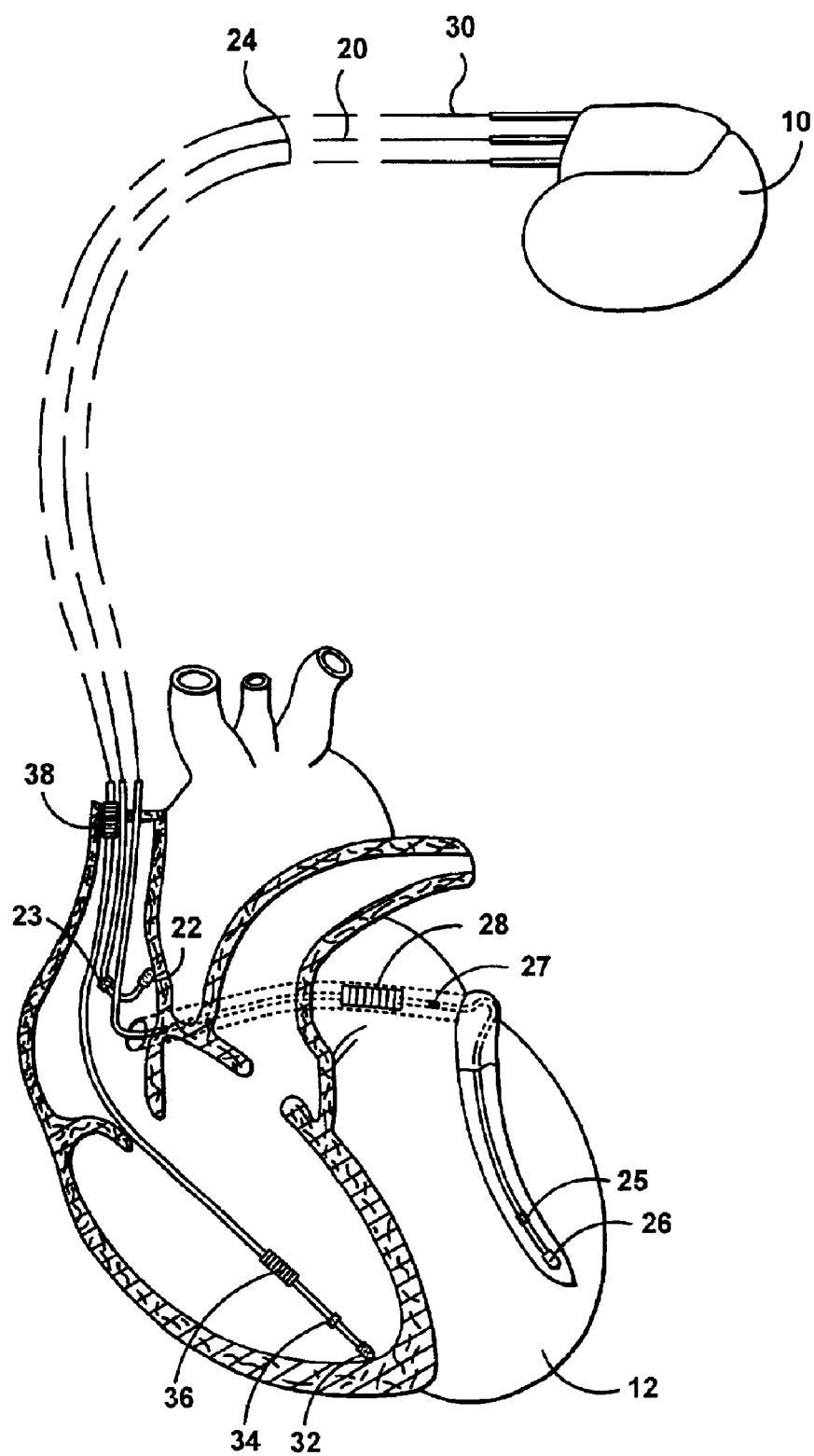
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The right atrial lead 20 may also have an atrial ring electrode 23 to allow bipolar stimulation or sensing in combination with the atrial tip electrode 22. In the present invention, right atrial stimulation is preferably delivered using the atrial tip electrode 22, and the propagating evoked response is sensed using the atrial ring electrode 23.

To sense the left atrial and ventricular cardiac signals and to provide left-chamber stimulation therapy, the stimulation device 10 is coupled to a "coronary sinus" lead 24 designed for placement in the "coronary sinus region" via the coronary sinus ostium so as to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to: receive atrial and ventricular cardiac signals; deliver left ventricular pacing therapy using at least a left ventricular tip electrode 26 for unipolar configurations or in combination with left ventricular ring electrode 25 for bipolar configurations; deliver left atrial pacing therapy using at least a left atrial ring electrode 27, and shocking therapy using at least a left atrial coil electrode 28. In the present invention, the left ventricular tip electrode 26 is preferably used for stimulation, and the left ventricular ring electrode 27 is preferably used for sensing the evoked response.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the right atrium and/or superior vena cava. Accordingly, the right ventricular lead 30 is capable of receiving cardiac signals, and delivering stimulation in the form of pacing and shock therapy to the right ventricle. In the present invention, the right ventricular tip electrode 32 is preferably used for stimulation, and the right ventricular ring electrode 34 is preferably used for sensing the propagating evoked response.

Figure 2:
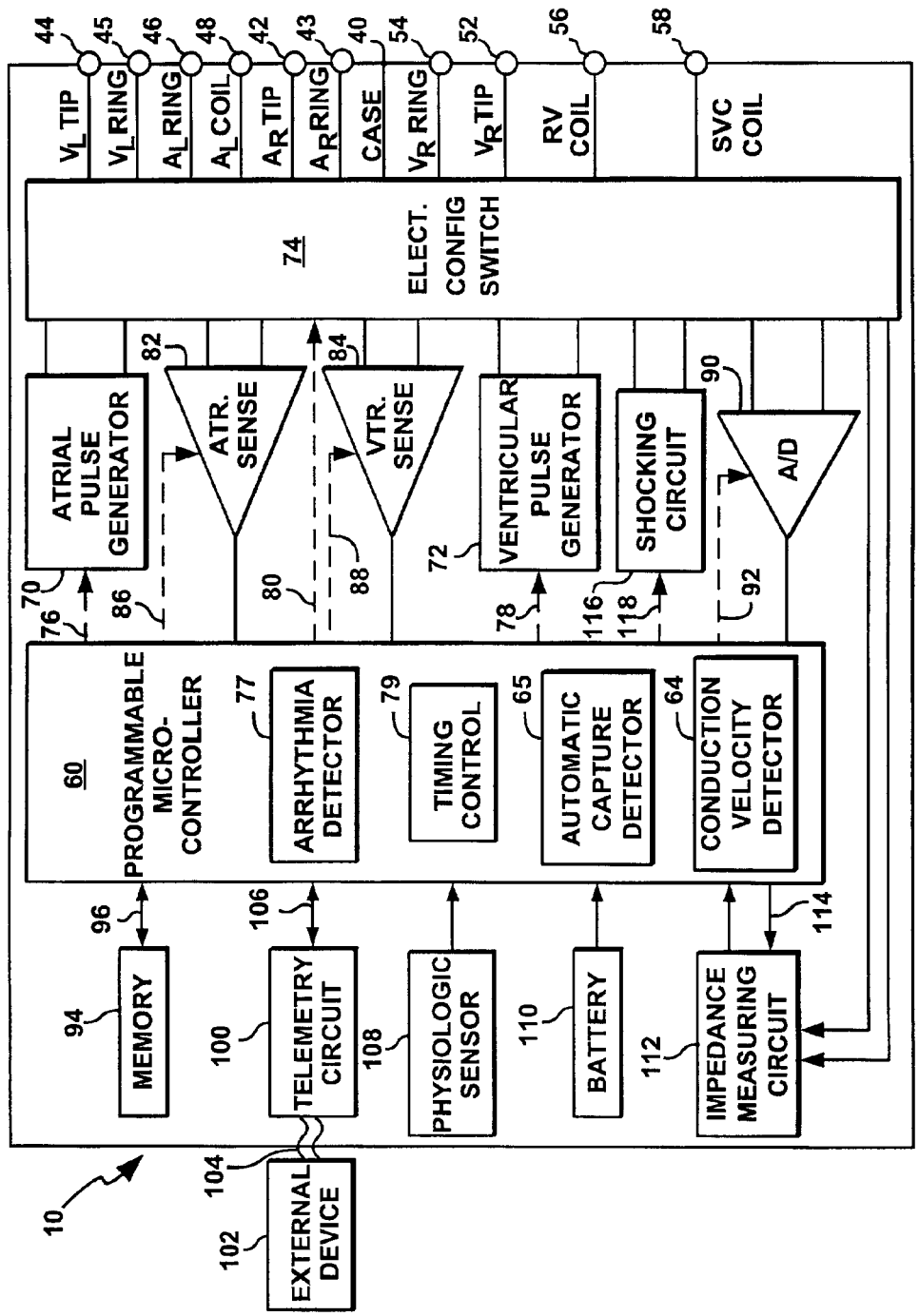
FIG. 2 is a functional block diagram of the multi-chamber implantable stimulation device of FIG. 1, illustrating the basic elements that provide pacing stimulation, cardioversion, and defibrillation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for defibrillation shocking purposes. The housing 40 further includes a connector having a plurality of terminals 42, 43, 44, 45, 46, 48, 52, 54, 56, and 58 (shown schematically and, for convenience, the names of the electrodes to which they are connected are shown next to the corresponding terminals). As such, to achieve right atrial sensing and stimulation, the connector includes at least a right atrial tip terminal ($A_R$ TIP) 42 adapted for connection to the atrial tip electrode 22. The connector also includes a right atrial ring terminal ($A_R$ RING) 43 for connection to the right atrial ring electrode 23.

To achieve left chamber sensing, pacing, and shocking, the connector includes at least a left ventricular tip terminal ($V_L$ TIP) 44, a left ventricular ring terminal ($V_L$ RING) 45, a left atrial ring terminal ($A_L$ RING) 46, and a left atrial shocking coil terminal ($A_L$ COIL) 48, which are adapted for connection to the left ventricular tip electrode 26, the left ventricular ring electrode 25, the left atrial ring electrode 27, and the left atrial coil electrode 28, respectively.

To support right ventricular sensing, pacing and shocking, the connector further includes a right ventricular tip terminal ($V_R$ TIP) 52, a right ventricular ring terminal ($V_R$ RING) 54, a right ventricular shocking coil terminal (RV COIL) 56, and an SVC shocking coil terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. The microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein.

FIG. 2 illustrates an atrial pulse generator 70 and a ventricular pulse generator 72 that generate stimulation pulses for delivery by the right atrial lead 20, the right ventricular lead 30, and/or the coronary sinus lead 24 via a switch 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g. pacing rate, atrio-ventricular (AV) delay, atrial interchamber (A—A) delay, or ventricular interchamber (V—V) delay, etc.), as well as to keep track of the timing of refractory periods, noise detection windows, evoked response windows, alert intervals, marker channel timing, etc.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g. unipolar, bipolar, cross-chamber, etc.) by selectively closing the appropriate combination of switches. Atrial sensing circuits 82 and ventricular sensing circuits 84 may also be selectively coupled to the right atrial lead 20, coronary sinus lead 24, and the right ventricular lead 30, through the switch 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch 74 determines the "sensing polarity" of the cardiac signal by selectively closing the appropriate switches. In this way, the clinician may program the sensing polarity independent of the stimulation polarity.

Each of the atrial sensing circuit 82 or the ventricular sensing circuit 84 preferably employs one or more low power, precision amplifiers with programmable gain and automatic gain or sensitivity control, bandpass filtering, and a threshold detection circuit, to selectively sense the cardiac signal of interest. The automatic sensitivity control enables the stimulation device 10 to deal effectively with the difficult problem of sensing the low amplitude signal characteristics of atrial or ventricular fibrillation.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry, and the timing of any blocking circuitry coupled to the inputs of the atrial and ventricular sensing circuits 82 and 84.

For arrhythmia detection, the stimulation device 10 includes an arrhythmia detector 77 that utilizes the atrial and ventricular sensing circuits 82 and 84 to sense cardiac signals, for determining whether a rhythm is physiologic or pathologic. As used herein "sensing" refers to the process of noting an electrical signal. "Detection" refers to the step of confirming that the sensed electrical signal as the signal being sought by the detector. As an example, "detection" applies to the detection of both proper rhythms (i.e., "R wave" or "R wave") as well as improper dysrhythmias including arrhythmia and bradycardia (e.g., detection of the absence of a proper rhythm.)

The timing intervals between sensed events (e.g. P-waves, R-waves, and depolarization signals associated with fibrillation which are sometimes referred to as "F-waves" or "Fib-waves") are then classified by the arrhythmia detector 77 by comparing them to a predefined rate zone limit (e.g. bradycardia, normal, low rate ventricular tachycardia, high rate ventricular tachycardia, and fibrillation rate zones) and various other characteristics (e.g. sudden onset, stability, physiologic sensors, and morphology, etc.), in order to determine the type of remedial therapy that is needed (e.g. bradycardia pacing, anti-tachycardia stimulation, cardioversion shocks or defibrillation shocks, collectively referred to as "tiered therapy").

Cardiac signals are also applied to the inputs of a data acquisition system 90, which is depicted as an analog-to-digital (A/D) converter for simplicity of illustration. The data acquisition system 90 is configured to acquire intracardiac electrogram (EGM) signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture". In the embodiment shown in FIG. 2, the microcontroller 60 includes an automatic capture detector 65 that searches for an evoked response signal following a stimulation pulse during a "detection window" set by timing control circuitry 79. The microcontroller 60 enables the data acquisition system 90 via control signal 92 to sample the cardiac signal that falls in the capture detection window. The sampled signal is evaluated by automatic capture detector 65 to determine if it is an evoked response signal based on its amplitude, peak slope, morphology or another signal feature or combination of features. The detection of an evoked response during the detection window indicates that capture has occurred.

Capture detection may occur on a beat-by-beat basis or on a sampled basis. When loss of capture is detected, a safety, back-up pulse is delivered shortly after the primary pulse in order to prevent asystole. Preferably, a capture threshold search is then performed in order to re-determine the threshold and appropriately adjust the stimulation pulse output. A capture threshold search may also be performed on a periodic basis, preferably once a day during at least the acute phase (e.g., the first 30 days) and less frequently thereafter. A capture threshold search would begin at a desired starting point (either a high output level or the level at which capture is currently occurring) and continue by decreasing the output level until capture is lost. The output level is then increased again until capture is regained. The lowest output level at which sustained capture is regained is known as the capture threshold. Thereafter, the stimulation output is adjusted to a level equal to the capture threshold plus a working margin.

In accordance with the present invention, capture detection algorithms and circuitry may also be used alone or in conjunction with special circuitry shown as a conduction velocity detector 64 for detecting an evoked response for the purposes of measuring a myocardial conduction time. Methods will be described herein for determining the time between a delivered stimulation pulse and the detection of the subsequent evoked response after it has propagated to a sensing electrode. This time interval is a measure of myocardial conduction time and is linearly proportional to the myocardial conduction velocity by a factor equal to the distance between the stimulating electrode and the sensing electrode.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, stimulation pulse amplitude, pulse duration, electrode polarity, rate, sensitivity, automatic features, arrhythmia detection criteria, and the amplitude, waveshape and vector of each stimulation pulse to be delivered to the patient's heart 12 within each respective tier of therapy.

The memory 94 may further be used for storing cardiac data. In accordance with the present invention, long-term myocardial conduction velocity data will be stored in memory 94 to allow later analysis by a physician. Advantageously, stored cardiac data may be non-invasively downloaded to an external device 102 through a telemetry circuit 100. A log or histogram of long-term conduction velocity data may be downloaded to the external device 102 and displayed in a tabular or graphical format for analysis by a physician.

The operating parameters of the stimulation device 10 may be non-invasively programmed into the memory 94 through the telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

The stimulation device 10 may further include a physiologic sensor 108, commonly referred to as a "rate-responsive" sensor because it is typically used to adjust stimulation rate according to the exercise state of the patient. However, the physiological sensor 108 may further be used to detect changes in cardiac output, changes in the physiological condition of the heart, or diurnal changes in activity (e.g. detecting sleep and wake states). Accordingly, the microcontroller 60 responds by adjusting the various stimulation parameters (such as rate, AV Delay, V—V Delay, etc.) at which the atrial and ventricular pulse generators 70 and 72 generate stimulation pulses.

While the physiologic sensor 108 is shown as being included within the stimulation device 10, it is to be understood that the physiologic sensor 108 may alternatively be external to the stimulation device 10, yet still be implanted within, or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors of blood oxygen content, blood pH, respiration rate and/or minute ventilation, ventricular gradient, etc. Any sensor may be used which is capable of sensing a physiological parameter that corresponds to the exercise state of the patient.

The stimulation device 10 additionally includes a power source such as a battery 110 that provides operating power to all the circuits shown in FIG. 2. For the stimulation device 10, which employs shocking therapy, the battery 110 should be capable of operating at low current drains for long periods of time, preferably less than 10 $\mu$A, and also be capable of providing high-current pulses when the patient requires a shock pulse, preferably, in excess of 2 A, at voltages above 2 V, for periods of 10 seconds or more. The battery 110 preferably has a predictable discharge characteristic so that elective replacement time can be detected.

As further illustrated in FIG. 2, the stimulation device 10 is shown to include an impedance measuring circuit 112 which is enabled by the microcontroller 60 by control signal 114. The known uses for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used for impedance measurements.

If it is a function of the stimulation device 10 to operate as an implantable cardioverter/defibrillator (ICD) device, it must detect the occurrence of an arrhythmia, and automatically apply an appropriate electrical stimulation or shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high (11 to 40 joules) energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
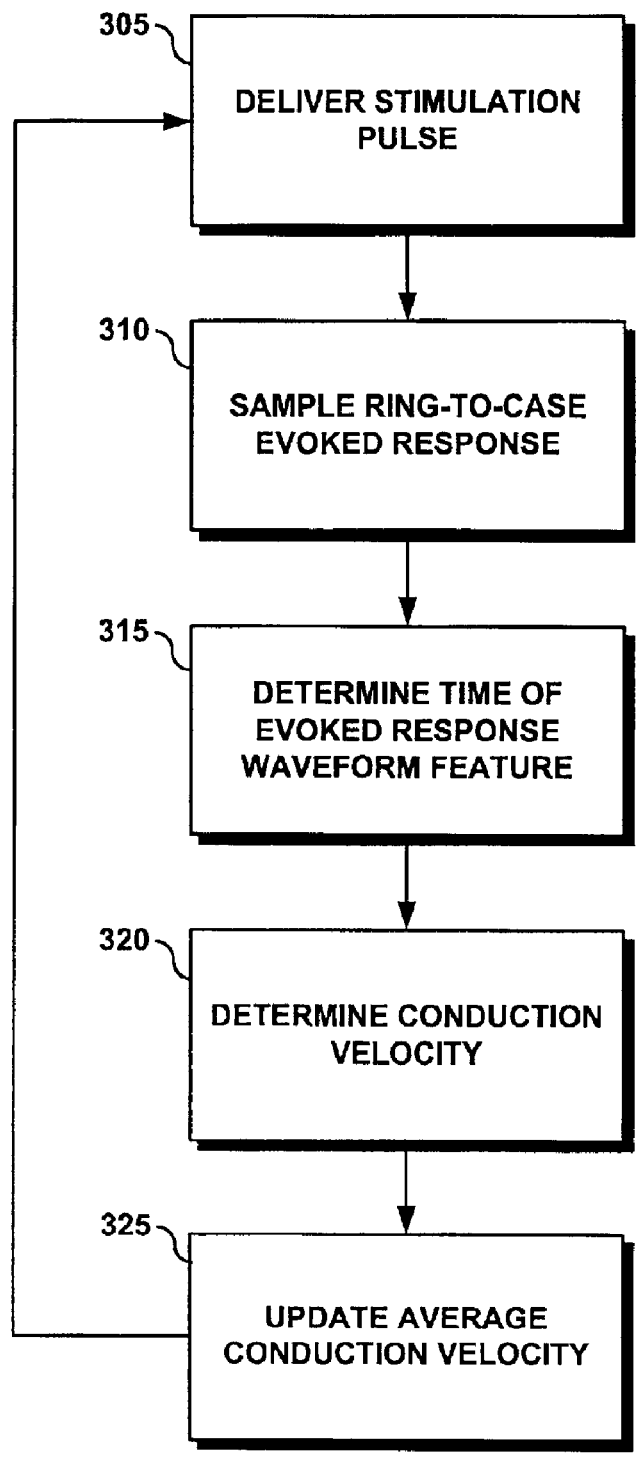
FIG. 3 is a flow chart providing an overview of the operations included in one embodiment of the present invention for measuring myocardial conduction time and storing a long-term average myocardial conduction velocity.

In FIG. 3, a flow chart is shown describing an overview of the operation and novel features implemented in one embodiment of the device 10 for measuring myocardial conduction time and storing a long-term running average of the conduction velocity. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The method 300 begins at step 305 when a stimulation pacing pulse is delivered by either atrial pulse generator 70 or ventricular pulse generator 72. The method 300 may be used in any heart chamber and may be used in more than one heart chamber in a given patient such that long-term average conduction velocities may be acquired for atrial and ventricular heart chambers. The stimulation pacing pulse is preferably delivered using a tip electrode so that, at step 310, the evoked response may be sampled by data acquisition system 90 using a unipolar ring-to-case sensing configuration.

The stimulation pulse energy delivered at step 305 is sufficient to elicit an evoked response. An evoked response is a depolarization of the myocardial cells due to a stimulation pulse. The depolarization wavefront evoked by the stimulation pulse will take a certain amount of time to propagate through the myocardial tissue to the ring electrode. The time required for the depolarization wavefront to propagate from the tip electrode to the ring electrode is a function of the myocardial tissue conduction velocity and the inter-electrode distance:

conduction time=tissue conduction velocity×inter-electrode distance

The inter-electrode distance, which is the distance between the tip electrode and the ring electrode, is preferably a distance that allows the evoked response to be detected after the polarization signal associated with the stimulation pacing pulse has substantially decayed. For example, Model 1474T pacing lead available from St. Jude Medical, Inc. has a tip-to-ring spacing that allows the ring-to-case evoked response to be detected on the order of 15 to 80 ms after the stimulation pacing pulse.

At step 315, conduction velocity detector 64 detects a predetermined depolarization waveform feature and determines the time of its occurrence relative to the time of the stimulation pulse. The waveform feature is preferably a peak negative slope, but may be any feature detectable from the sampled depolarization waveform such as a peak amplitude, a zero crossing, or an inflection point. The time of the waveform feature is used as a timing marker for determining the conduction time.

The myocardial conduction time is then determined at step 320 as the difference between the time of the stimulation pacing pulse delivery and the time of the detected depolarization waveform feature. At step 320, additional arithmetic may also be performed to calculate the conduction velocity by dividing the conduction time by the known inter-electrode distance.

At step 325, the long-term running average conduction velocity is updated. This long-term average is determined by averaging the conduction velocities determined from a large number of consecutive paced cardiac cycles from which a conduction time measurement has been made. Typically, a long-term average conduction velocity will be calculated from greater than 100 conduction time measurements, preferably from 500 to 5,000 conduction time measurements.

In one embodiment, each conduction time measurement is stored in memory, and, after a given number of conduction time measurements have been made, a new long-term average is calculated and stored. In another embodiment, a running average may be updated upon each new conduction time measurement using a given number of the most recent conduction time measurements. This running average may then be stored in memory 94 every time it is updated or on a periodic basis.

In a given patient the tip-to-ring spacing will remain fixed as long as the lead is not moved or replaced. Changes in the myocardial conduction velocity will therefore be linearly proportional to changes in conduction time. Thus, either the average conduction time or average conduction velocity may be used in the present invention; whichever is deemed most appropriate for the desired application or diagnostic. In most cases, either parameter will be appropriate since they are linearly proportional to each other. When using conduction time, the need to know the tip-to-ring distance and the related arithmetic required to perform the conversion from conduction time to conduction velocity made at step 320 are not necessary.

In another embodiment, the effect of heart rate on myocardial conduction time is taken into account. Rate-responsive pacing or dynamic overdrive pacing algorithms automatically adjust the pacing rate. During rate-responsive pacing, the rate is automatically increased or decreased to meet the metabolic needs of the patient based on signals from the physiological sensor 108. During dynamic overdrive pacing, the pacing rate is adjusted to be greater than the sensed intrinsic rate. Changes in pacing rate due to such algorithms may influence the myocardial conduction velocity. Therefore, multiple average conduction velocities associated with a given pacing rate, or pacing rate range, may be stored simultaneously. Conduction time measurements may be stored in a histogram format with each histogram bin assigned to a given pacing rate or pacing rate range. The long-term average conduction velocity is then calculated for each pacing rate range.

Figure 4:
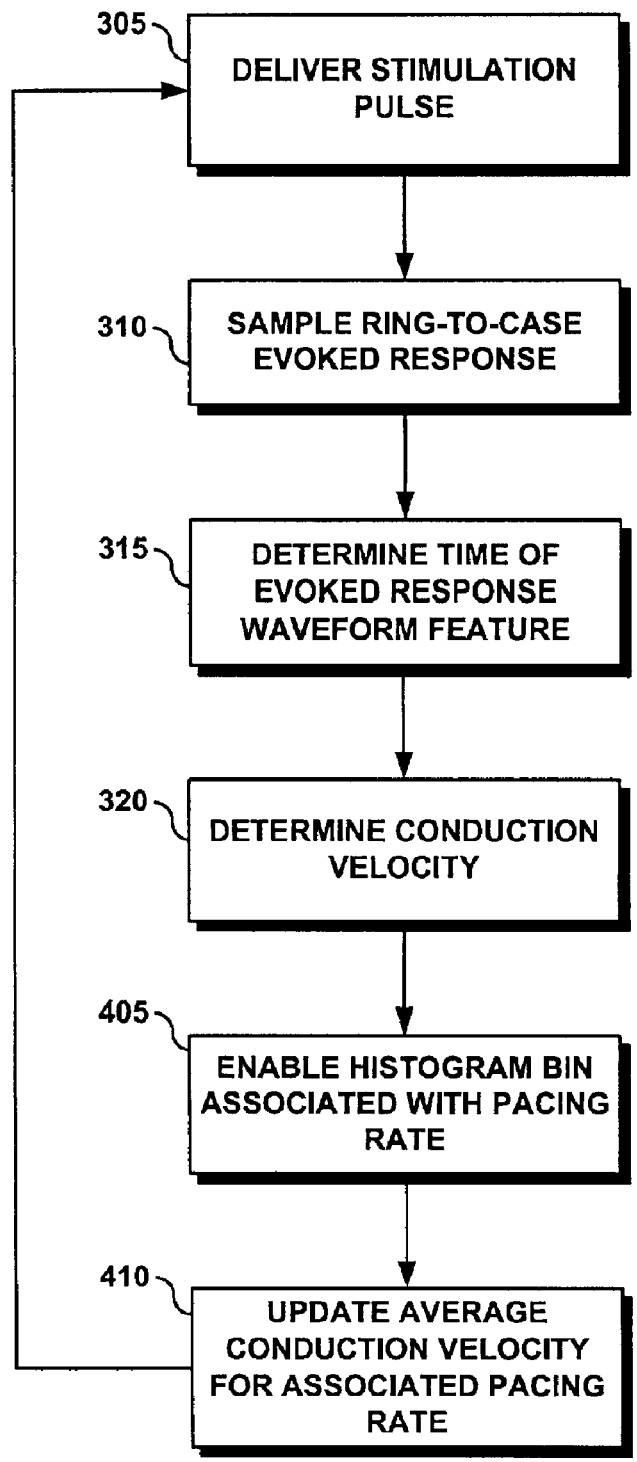
FIG. 4 is a flow chart providing an overview of the operations included in another embodiment of the present invention for measuring myocardial conduction time and storing multiple long-term average myocardial conduction velocities associated with multiple heart rates.

This embodiment is outlined by the flow chart shown in FIG. 4. During steps 305 through 320, a conduction time is measured and a conduction velocity calculated, if desired, exactly as previously described for method 300 of FIG. 3. At step 405, a histogram bin assigned to the current pacing rate is enabled. The average conduction velocity stored in this histogram bin is updated at step 410 using the newly measured conduction velocity.

In another embodiment, the conduction time measurement is converted to a ratio, a product, or a function of the heart rate (i.e., conduction time/heart rate, heart rate*conduction time, or corrected conduction time=f(heart rate)*conduction time). The long term running average is then calculated from the conduction time to heart rate ratios.

In yet another embodiment, the effect of pacing pulse energy on conduction time is taken into account. Increasing stimulation pulse amplitudes can increase the size of the "virtual cathode", defined to be the perimeter of the area of tissue that is depolarized with a pacing pulse. As the pacing pulse amplitude is increased, the reach of the electric field generated by the pulse increases, such that myocardial cells further from the electrode are depolarized. When this happens, increased stimulation pulse amplitudes may result in shorter measured conduction times because the depolarization wavefront will now start out closer to the ring electrode. These measurements would falsely indicate a physiologic change in the state of the myocardial tissue propagating the depolarization. Since long-term averages may incorporate a wide range of stimulation pulses, due to threshold changes or automatic capture algorithms, the effect of pacing pulse energy can be compensated for by associating each measured conduction time with the pacing pulse amplitude used at the time of measurement. This association or correction can be as for heart rate: a product or a function of the stimulating pacing pulse energy (pulse energy times conduction time, corrected conduction time=f (pulse energy)*conduction time).

A shift in the long-term average conduction velocity (or time) may indicate to a clinician a change in the patient's disease state, response to a drug therapy or a response to a pacing therapy. Thus, the long-term average conduction velocity may be used as a feedback parameter in optimizing drug or pacing therapy.

Long-term averages may be compared to one or more previous long-term averages in order to detect a change in myocardial conduction. Alternatively, a reference value may be obtained by computing a conduction velocity average over a much longer time period than the long-term average, for example an average of ten to fifty times more conduction velocity measurements than the long-term average. The long-term averages may then be compared to this reference value in order to detect shifts in the myocardial conduction velocity.

In another embodiment, a multipolar lead may be used having a pacing tip electrode and multiple sensing ring electrodes spaced along the length of the lead in contact with different myocardial tissue sites to allow detection of a propagating depolarization waveform at several locations. The time at which a waveform feature is detected at each sensing electrode may be determined such that the conduction time of multiple tissue segments may be determined. The methods used for this embodiment would be similar to the methods 300 or 400 used for measuring a single conduction time. The same method would be applied to multiple sensing electrodes simultaneously.

Identifying deviations in the conduction time associated with individual tissue segments may aid in the detection and diagnosis of local ischemia. Stimulation pacing parameters or electrode configuration selection may be adjusted to avoid or alleviate the locally ischemic region or to optimize the stimulation response in the presence of a slowly conducting region.

Thus, a system and method for monitoring the long-term average myocardial conduction velocity has been described. While detailed descriptions of specific embodiments of the present invention have been provided, it would be apparent to those reasonably skilled in the art that numerous variations of the methods described herein are possible in which the concepts of the present invention may readily be applied. The descriptions provided herein are for the sake of illustration and are not intended to be exclusive.

What is claimed is:

1. A method of monitoring a conduction velocity of a myocardial tissue for use in a cardiac stimulation device, comprising:

delivering a stimulus that causes an evoked myocardial depolarization using a stimulating electrode located on a multipolar lead;

detecting the evoked myocardial depolarization using a sensing electrode located on the multipolar lead that is separated by a predetermined distance from the stimulating electrode;

determining a time of occurrence of a feature of the evoked myocardial depolarization;

calculating a myocardial conduction time as a difference between a time at which the stimulus was delivered and the time of the depolarization signal feature; and calculating the conduction velocity by dividing the myocardial conduction time by an inter-electrode distance between the stimulating electrode and the sensing electrode.

2. The method according to claim 1, further comprising calculating a long-term average myocardial conduction time by averaging a given number of conduction time measurements.

3. The method according to claim 2, further comprising calculating a long-term average myocardial conduction velocity by dividing the long-term average myocardial conduction time by the inter-electrode distance.

4. The method according to claim 2, further comprising storing the long-term average myocardial conduction time.

5. The method according to claim 1, wherein the inter-electrode distance allows the evoked myocardial depolarization to be detected within approximately 15 to 150 ms after the time at which the stimulus was delivered.

6. The method according to claim 5, wherein the feature of the evoked myocardial depolarization is any of:

a peak negative slope;

a peak positive slope;

a peak amplitude;

a zero crossing; or an inflection point.

7. The method according to claim 5, wherein calculating the long-term average myocardial conduction time comprises averaging at least 100 conduction time measurements.

8. The method according to claim 1, further comprising converting the myocardial conduction time as a function of a heart rate.

9. The method according to claim 1, further comprising converting the myocardial conduction time as a ratio of the myocardial conduction time to a stimulus rate.

10. The method according to claim 1, further comprising calculating a plurality of long-term myocardial conduction time averages corresponding to a plurality of heart rate ranges.

11. The method according to claim 1, further comprising calculating a plurality of long-term myocardial conduction time averages corresponding to a plurality of stimulation pulse amplitudes.

12. The method according to claim 1, further comprising downloading the long-term average myocardial conduction time to an external device.

13. The method according to claim 1, further comprising using the conduction velocity for monitoring any of:

a disease state;

a response to a medical therapy;

a response to a stimulation therapy; or a local ischemia.

14. The method according to claim 11, further comprising automatically adjusting a stimulation parameter based on the long-term average myocardial conduction time.

15. The method according to claim 2, wherein calculating the long-term average myocardial conduction time comprises calculating and storing conduction time averages for two or more myocardial tissue segments by:

sensing a unipolar evoked depolarization signal from two or more sensing electrodes located on a multipolar lead that are separated by a distance from the stimulating electrode;

determining the time of occurrence of the feature of the evoked myocardial depolarization at each sensing electrode;

calculating a myocardial conduction time associated with each sensing electrode; and calculating a long-term average myocardial conduction time associated with each sensing electrode by averaging a given number of recent conduction time measurements made for each sensing electrode.

16. A cardiac stimulation device capable of monitoring a conduction velocity of a myocardial tissue, comprising:

a pulse generator that generates stimulation pulses;

a stimulating electrode, located on a multipolar lead that is connected to the pulse generator, to selectively deliver the stimulation pulses for causing an evoked myocardial depolarization;

a sensing electrode located on the multipolar lead at a predetermined distance from the stimulating electrode, to detect the evoked myocardial depolarization;

a conduction velocity detector that determines a time of occurrence of a feature of the evoked myocardial depolarization;

wherein the conduction velocity detector calculates a myocardial conduction time as a difference between a time at which the stimulus was delivered and the time of the depolarization signal feature, and further calculates the conduction velocity by dividing the myocardial conduction time by an inter-electrode distance between the stimulating electrode and the sensing electrode.

17. The cardiac stimulation device according to claim 16, wherein the conduction velocity detector further calculates a long-term average myocardial conduction time by averaging a given number of conduction time measurements.

18. The cardiac stimulation device according to claim 17, wherein the conduction velocity detector further calculates a long-term average myocardial conduction velocity by dividing the long-term average myocardial conduction time by the inter-electrode distance.

19. The cardiac stimulation device according to claim 17, further comprising data storage for storing the long-term average myocardial conduction time.

20. The cardiac stimulation device according to claim 16, wherein the inter-electrode distance is set to allow the evoked myocardial depolarization to be detected within approximately 15 to 150 ms after the time at which the stimulation pulses were delivered.

21. The cardiac stimulation device according to claim 20, wherein the feature of the evoked myocardial depolarization is any of:

a peak negative slope;

a peak positive slope;

a peak amplitude;

a zero crossing; or an inflection point.

22. The cardiac stimulation device according to claim 20, wherein the long-term average myocardial conduction time is an average of at least 100 conduction time measurements.

23. The cardiac stimulation device according to claim 16, wherein the conduction velocity detector converts the myocardial conduction time as a function of a heart rate.

24. The cardiac stimulation device according to claim 16, wherein the conduction velocity detector converts the myocardial conduction time as a ratio of the myocardial conduction time to a stimulus rate.

25. The cardiac stimulation device according to claim 17, further comprising a controller that automatically adjusts a stimulation parameter based on the long-term average myocardial conduction time.

26. A cardiac stimulation device for monitoring a conduction velocity of a myocardial tissue, comprising:
   means for delivering a stimulus that causes an evoked myocardial depolarization using a stimulating electrode means located on a multipolar lead;
   means for detecting the evoked myocardial depolarization using a sensing electrode means located on the multipolar lead that is separated by a predetermined distance from the stimulating electrode means;
   means for determining a time of occurrence of a feature of the evoked myocardial depolarization; and
   means for calculating a myocardial conduction time as a difference between a time at which the stimulus was delivered and the time of the depolarization signal feature, and for further calculating the conduction velocity by dividing the myocardial conduction time by an inter-electrode distance between the stimulating electrode means and the sensing electrode means.

27. The cardiac stimulation device according to claim 26, wherein the calculating means further calculates a long-term average myocardial conduction time by averaging a given number of conduction time measurements.

28. The cardiac stimulation device according to claim 27, wherein the calculating means further calculates a long-term average myocardial conduction velocity by dividing the long-term average myocardial conduction time by the inter-electrode distance.

29. The cardiac stimulation device according to claim 27, further comprising memory means for storing the long-term average myocardial conduction time.

30. The cardiac stimulation device according to claim 26, wherein the inter-electrode distance is set to allow the evoked myocardial depolarization to be detected within approximately 15 to 150 ms after the time at which the stimulus was delivered.

31. The cardiac stimulation device according to claim 30, wherein the feature of the evoked myocardial depolarization is any of:
   a peak negative slope;
   a peak positive slope;
   a peak amplitude;
   a zero crossing; or
   an inflection point.

32. The cardiac stimulation device according to claim 26, further comprising means for converting the myocardial conduction time as a function of a heart rate.

33. The cardiac stimulation device according to claim 26, further comprising means for converting the myocardial conduction time as a ratio of the myocardial conduction time to a stimulus rate.

* * * * *